United States Patent
Reese et al.

(10) Patent No.: US 9,517,361 B2
(45) Date of Patent: Dec. 13, 2016

(54) CRYSTAL ENCAPSULATED NANOPARTICLES METHODS AND COMPOSITIONS

(71) Applicants: David A. Reese, West Lafayette, IN (US); Steven F. Son, West Lafayette, IN (US); Allen Hoe Yan, West Lafayette, IN (US)

(72) Inventors: David A. Reese, West Lafayette, IN (US); Steven F. Son, West Lafayette, IN (US); Allen Hoe Yan, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 848 days.

(21) Appl. No.: 13/652,051

(22) Filed: Oct. 15, 2012

(65) Prior Publication Data
US 2015/0175495 A1    Jun. 25, 2015

Related U.S. Application Data

(60) Provisional application No. 61/547,982, filed on Oct. 17, 2011.

(51) Int. Cl.
*A61Q 19/00*    (2006.01)
*A61K 9/51*    (2006.01)
(Continued)

(52) U.S. Cl.
CPC ............ *A61Q 19/00* (2013.01); *A61K 8/0241* (2013.01); *A61K 8/8194* (2013.01); *A61K 9/16* (2013.01);
(Continued)

(58) Field of Classification Search
CPC .......... A61K 9/14; A61K 9/50; A61K 9/5192; A61K 8/0241; A61K 8/02; C06B 45/30; C06B 45/18; C06B 45/02; C06B 45/32; A61Q 19/00
(Continued)

(56) References Cited

U.S. PATENT DOCUMENTS 3,523,839 A    8/1970    Shechter et al.
3,586,645 A *  6/1971    Granger ................... C08J 9/04
                                                      264/51
(Continued)

OTHER PUBLICATIONS

Z. Ma et al., "Preparation and characterization of superfine ammonium perchlorate (AP) crystals through ceramic membrane antisolvent crystallization," J. of Crystal Growth, 2009, vol. 331, pp. 4575-4580.
(Continued)

*Primary Examiner* — Aileen B Felton
(74) *Attorney, Agent, or Firm* — Pauley Erickson & Kottis

(57) ABSTRACT

The invention provides methods for encapsulating nanometric particles inside of micro-sized crystals. An exemplary embodiment involves crystallizing a solution including nanometric particles, a micelle-forming material, a nonpolar dispersant for the micelle-forming material and a crystal-forming material to form crystal-encapsulated nanometric particles. Also provided are compositions or materials which include or are formed using the crystal encapsulated nanoparticles, such compositions and materials can include propellants, cosmetics, composite structures, energetics, and pharmaceutical compositions/materials.

18 Claims, 3 Drawing Sheets

(51) Int. Cl.
- *A61K 8/02* (2006.01)
- *A61K 9/16* (2006.01)
- *C06B 45/18* (2006.01)
- *A61Q 1/02* (2006.01)
- *A61K 8/81* (2006.01)
- *C06B 45/02* (2006.01)
- *C06B 45/32* (2006.01)

(52) U.S. Cl.
CPC ........... *A61K 9/5115* (2013.01); *A61K 9/5192* (2013.01); *A61Q 1/02* (2013.01); *C06B 45/02* (2013.01); *C06B 45/18* (2013.01); *C06B 45/32* (2013.01); *A61K 2800/10* (2013.01); *A61K 2800/413* (2013.01); *A61K 2800/624* (2013.01); *Y10T 428/2991* (2015.01)

(58) Field of Classification Search
USPC .................................. 424/46, 490; 977/915
See application file for complete search history.

(56) References Cited

U.S. PATENT DOCUMENTS

| | | | |
|---|---|---|---|
| 3,685,163 A | | 8/1972 | Olt |
| 3,706,608 A | * | 12/1972 | Geisler ............... C06B 21/0083 149/19.9 |
| 3,892,610 A | * | 7/1975 | Huzinec ............... C01B 11/185 149/113 |
| 3,976,521 A | | 8/1976 | Boyd et al. |
| 4,944,816 A | * | 7/1990 | Sayles .................... C06B 33/08 149/19.8 |
| 5,356,978 A | * | 10/1994 | Garrison .................. C08J 3/215 523/333 |
| 2006/0083694 A1 | * | 4/2006 | Kodas .................. B01J 13/0043 424/46 |
| 2010/0104832 A1 | * | 4/2010 | Messe .................... C08L 63/00 428/201 |
| 2010/0323884 A1 | * | 12/2010 | Roldan Cuenya ..... B01D 53/88 502/339 |
| 2013/0164223 A1 | * | 6/2013 | Jeon .................. A61K 49/1839 424/9.322 |

OTHER PUBLICATIONS

S.U. Tanrikulu et al., "The growth and dissolution of ammonium perchlorate crystals in a fluidized bed crystallizer," J. of Crystal Growth, 1999, vol. 194, pp. 220-227.

* cited by examiner

CRYSTAL ENCAPSULATED NANOPARTICLES METHODS AND COMPOSITIONS

CROSS REFERENCE TO RELATED APPLICATIONS

This application claims priority to U.S. Provisional Patent Application 61/547,982, filed 17 Oct. 2011, and titled "A METHOD OF ENCAPSULATING NANOPARTICLES IN CRYSTALS AND COMPOSITIONS THEREOF." That priority application is hereby incorporated by reference herein and is made a part hereof, including but not limited to those portions which specifically appear hereinafter.

STATEMENT REGARDING FEDERALLY SPONSORED RESEARCH OR DEVELOPMENT

This invention was made with government support under FA9550-09-C-0176 awarded by the United States Air Force. The government has certain rights in the invention.

FIELD OF THE INVENTION

This invention generally pertains to the fields of crystal and solution chemistry and nanotechnology.

BACKGROUND OF THE INVENTION

Nanoparticles provide opportunities for technological advancement in various fields including, for example, propellants and energetics, composite structures, pharmaceuticals, and cosmetics. The acceptance and use of nanometric materials in at least some of these industries has to date, however, been generally limited as the extremely small sizes of these materials can present significant challenges in areas such as handling, dispersion, safety, and ultimate strength.

For example, while nanoparticles have shown promise for use in composite propellants, such as to significantly increase performance by altering the fundamental combustion process, their more widespread use or acceptance has been generally precluded by their tendency to agglomerate and their high surface area, which tend to limit the usefulness of the particles and the rheology of the propellant, respectively.

Further, with regard to energetic materials, besides propellants, there is a need and a desire to mitigate the occurrence of ignition of explosives which may occur due to "hot spot" formation inside the energetic crystals. Thus, there remains a need for processes or methods as well as specific materials or compositions that allow or permit the successful use and/or incorporation of nanoparticles in such applications.

Further, there has been increasing interest in the use of nanoparticles in applications such as in both pigments such as for cosmetic makeup and in efficient delivery for various medicines.

The possible biological impacts of the use of nanoparticles have, however, also become a growing cause for possible concern. For example, due to their extremely small size, the possible interaction between such particles and cell functioning can be of concern, as such interaction may interrupt vital processes.

Nanomaterials have also long been posited to enable extremely high strength composite materials, yet few (if any) of such high strength composite materials have ever been created or made in a lab environment.

U.S. Pat. No. 3,685,163 described a process where ultrafine crystals of pure ammonium perchlorate (AP) salt were prepared in a solution of water, n-heptane, and carboxylterminated polybutadiene prepolymer. This mixture was frozen, and the solvent sublimed from the blend to leave ultra-fine crystals.

SUMMARY OF THE INVENTION

The present invention provides methods and processes for making a composite of nanometric particles encapsulated by crystals as well as compositions comprising corresponding crystal-encapsulated nanometric particles.

In accordance with one aspect, one such method for making a composite of nanometric particles encapsulated by crystals involves crystallizing a solution including nanometric particles, a micelle-forming material, a nonpolar dispersant for the micelle-forming material and a crystal-forming material to form crystal-encapsulated nanometric particles.

In accordance with one specific embodiment there is provided a process for encapsulating nanometric iron oxide particles inside of micrometric ammonium perchlorate crystals. As described in greater detail below, one such process involves preparing a solution including nanometric iron oxide and ammonium perchlorate with a micelle-forming material and a polar dispersant for the micelle-forming material. The solution can subsequently be crystallized to form nanometric iron oxide particles encapsulated inside of micrometric ammonium perchlorate crystals.

In accordance another aspect, there is provided a composition comprising crystal-encapsulated nanometric particles. Such crystal-encapsulated nanometric particles can, in accordance with one embodiment include nanometric iron oxide particles encapsulated inside micrometric ammonium perchlorate crystals. Further, such crystal-encapsulated nanometric particles can be formed by a process wherein a solution that includes nanometric particles, a micelle-forming material, a nonpolar dispersant for the micelle-forming material and a crystal-forming material is crystallized to form the crystal-encapsulated nanometric particles.

Thus, it will be appreciated that the invention provides a process to capture nanometric particles inside of micron-size crystals. For example, the nanoparticles can be suspended in a polymer solution saturated with the desired crystalline material. The polymer coalesces around the nanoparticles to form micelles, which then function as nucleation sites for the formation of larger micron-size crystals around the nanoparticles. As presently envisioned, a primary application or use is to permit, facilitate or simplify the inclusion of nanoparticles in propellants. Additional applications or uses exist in fields such as composite structures, cosmetics, pharmaceuticals and energetic materials, for example.

As used herein, the terms "nanometric particles" and "nanoparticles" generally refer to small objects and materials that behave as a whole unit in terms of their transport and properties. Nanometric particles and nanoparticles are generally sized between 1 and 100 nanometers and are well known in the art.

Other objects and advantages will be apparent to those skilled in the art from the following detailed description taken in conjunction with the appended claims and drawings.

DETAILED DESCRIPTION OF THE INVENTION

The present invention significantly expands on the methodology of U.S. Pat. No. 3,685,163 (incorporated herein by reference) by introducing nanometric particles into the initial solution, which are then entrained and encapsulated during the crystallization process. Additionally, the new crystallization process outlined herein desirably can occur directly from liquid solution with a dissolved suitable salt, such as ammonium perchlorate (AP), hence increasing the production rate dramatically. In particular embodiments, the invention provides a process for the encapsulation of nanometric particles inside of micrometric crystals which forms a core-shell composite material, as well as the corresponding or associated compositions or materials.

Applicants believe that the prior inability to make or form extremely high strength composite materials with or via nanomaterials can be attributed to a lack of proper dispersion of the nanoparticles. As a result, agglomerated particles in the composite matrix may not or do not completely or properly interact with the matrix material, thus significantly decreasing the strength of the resulting composite material.

The present invention can advantageously serve to mitigate various concerns of regarding the use of nanoparticles in propellant compositions by containing the nanometric material inside of appropriate micron-size particles. For example, such materials or compositions can permit a desired more even dispersion of the nanometric material and can also reduce, minimize or eliminate the influence of the nanoscale particle surface area on the polymeric binder, while still maintaining intimate contact between fuel and oxidizer particles and thus retaining the potential performance increase provided by nanoparticles. In fact, improved performance via the materials and compositions of the invention are expected, as diffusional length scales for combustion will be decreased significantly, reducing the tendency for agglomeration and increasing efficiency.

Figure 1:
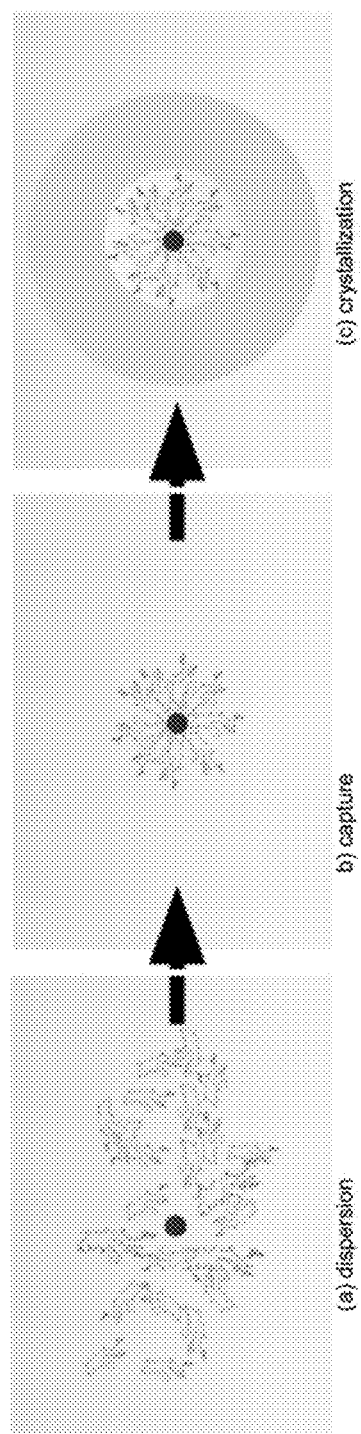
FIG. 1 is a schematic of the crystallization process, as envisioned on a nanometric scale, illustrating the dispersion, capture and crystallization of a nanometric particle in a polymer micelle.
Figure 2:
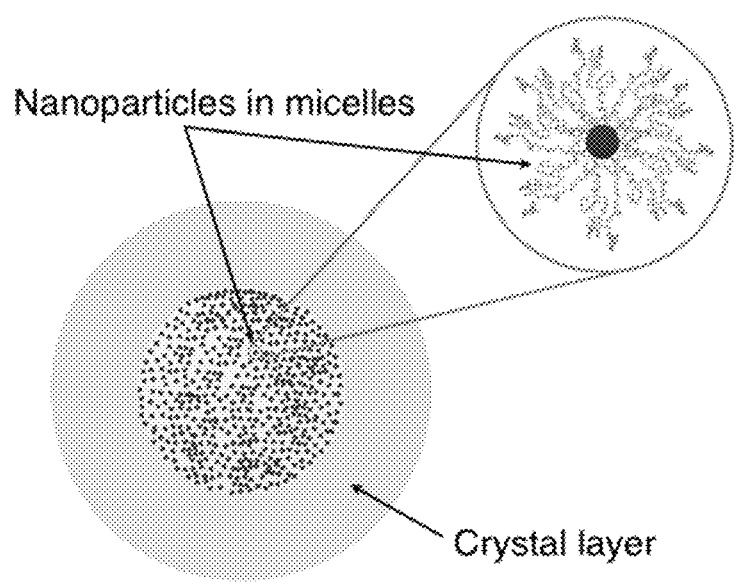
FIG. 2 is a schematic of final micelle-based crystal.

In accordance with one embodiment, a solution such as of a polar solvent (e.g., water) and a micelle-forming material/polymer (e.g., hydroxyl terminated polybutadiene, "HTPB") in tandem with a nonpolar dispersant for the polymer (e.g., pentane) is prepared. A crystal-forming material such as in the form of a salt (such as ammonium perchlorate, "AP") is introduced into the mixture and dissolved completely such as by mechanical agitation and/or temperature change. Nanometric particles of a selected material (e.g., nanometric iron oxide, "nanocat") are then added and dispersed such as by means of mechanical agitation. This agitation allows the particles to be somewhat deagglomerated and captured in micelles formed by the micelle-forming material or polymer (see FIG. 1). These micelles can then function as nucleation sites for salt crystal formation. The mixture is subsequently dried, such as via evaporation, to promote crystallization, and washed to clean excess nanomaterial from the surface of the crystals. A schematic of the final crystal can be seen in FIG. 2.

As identified above, nanoparticles as used herein are generally defined as small objects and materials that behave as a whole unit in terms of their transport and properties. Nanoparticles are generally sized between 1 and 100 nanometers and are well known in the art. Examples of suitable nanoparticle materials that can be used in the practice of the invention include iron oxide (nanocat), nanoaluminum, nanoboron, boron-nitride nanotubes (BNNT), nanodiamond, and the like.

A crystal-forming material or salt suitable for use in the practice of the invention is a material or salt which typically will form crystals, normally when dissolved either completely or sufficiently, around the nanoparticles according to the methodology described herein. Examples of suitable materials and salts include ammonium perchlorate, or numerous others such as SDS, TritonX-100, etc. When a suitable salt is used, it will form ionic crystals.

Suitable micelle-forming materials or polymers for use in the practice of the invention are those materials or polymers which generally facilitate the formation of crystal-encapsulated nanoparticles, through micelle formation with the nanoparticles. One example of such a micelle-forming material or polymer is hydroxl terminated polybutadiene (HTPB).

Suitable non-polar dispersant materials for use in the practice of the invention typically can include those dispersants which will act to disperse the micelle-forming material or polymer. Examples of such materials include petrol ether, hexane, benzene, heptane and toluene, and the like, and mixtures thereof.

In accordance with the invention, a solution including nanometric particles, a micelle-forming material, a nonpolar dispersant for the micelle-forming material and a crystal-forming material may and most typically will additionally include a suitable solvent such as may desirably serve to sufficiently drive the crystal-forming material or salt into solution to be able to form crystals around the nanoparticles. Suitable such solvents can typically include polar solvents such as water, acetone, methanol, ethanol, isopropanol, tetrahydrofuran, acetonitrile, I-propanol, pyridine, TMEDA, and the like, or mixtures thereof.

Generally, the nanoparticles are first suspended in a micelle-forming material or polymer solution saturated with the desired crystalline material. The material/polymer coalesces around the nanoparticles to form micelles, which then function as nucleation sites for the formation of larger micron-sized crystals around the nanoparticles.

While the invention has been described above making specific reference to the use of the invention in conjunction with or in propellant compositions, those skill in the art and guided by the teachings herein provided will understand and appreciate that the broader practice of the invention is not necessarily so limited.

For example, additional applications or uses of the present teachings herein described include in the fields of cosmetics and pharmaceuticals.

In the case of cosmetics, the encapsulation or wrapping of the nanoparticles in micron-scale crystals as herein described can allow the nanoparticles to be included in a composition such as for one or more of the specific properties thereof, such as for their optical properties, while desirably maintaining a barrier between the nanoparticle and the skin surface of the user. In the case of pharmaceuticals, the crystal structure materials herein described can allow for more precise delivery timing and increased compatibility.

Other applications can also benefit from the optical properties of nanoparticles. Further, encasing nanometric particles in transparent crystals may enable their use in practices which may currently be prohibited by virtue of their comparatively small size.

Additional applications of the developments herein described can include use in or as structural composite materials. For example, the invention desirably can provide an improved means of dispersing the nanoparticles in the composite by suspending the nanoparticles in crystals compatible with the matrix material. These crystals can separate and align the nanoparticles on a micron scale and with careful selection of crystal material, can either be dissolved out following matrix hardening or integrated with the matrix to form a part of the composite structure.

Still other applications for the developments herein described can include use in or as energetic materials. For example, by including or containing metallic nanoparticles inside of a crystal of energetic material, the location and intensity of the above-described "hot spots" inside energetic crystals, such as can lead to undesired ignition of explosives, can desirably be better or more appropriately controlled. As a result, such use may, for example, better provide or result in more highly controllable ignition such as by means of electromagnetic radiation.

In addition, it has been shown that when nanometals (Al in particular) are dispersed throughout an explosive, they can participate in at least some detonation reaction zones. However, in composite explosives (e.g., plastic bonded explosives—PBX), added nanofuels do not participate in the detonation reaction zone. Further, core-shell reactive crystal composites can be utilized in enhanced blast explosives (EBX). Further, nanoenergetics can potentially be encased in particles of sufficient mass to be thrown into the surrounding air, thus increasing the effectiveness of the EBX.

The present invention is described in further detail in connection with the following example(s) which illustrate or simulate various aspects involved in the practice of the invention. It is to be understood that all changes that come within the spirit of the invention are desired to be protected and thus the invention is not to be construed as limited by these example(s).

EXAMPLE(S)

In this example, a preparation in accordance with the composition set forth in Table 1 was prepared as described below.

TABLE 1

| Ingredient | Amount (g) |
|---|---|
| ammonium perchlorate | 1 |
| nanometric $Fe_2O_3$ | 0.1 |
| deionized water | 9.27 |
| n-pentane | 1.45 |
| R45M Hydroxyl-terminated polybutadiene (HTPB) | 0.05 |

The deionized water and ammonium perchlorate were first added to an Erlenmeyer flask and stirred to dissolve. Next, a solution containing the listed amount of n-pentane, HTPB, and nanometric $Fe_2O_3$ was prepared and added to the contents of the flask. The flask was placed on a stirrer/heating plate with the stir setting at 350 revolutions per minute and a temperature setting of 40° C. The flask was then placed under vacuum at 0.2 psia until the mixture was dry. Finally, using a spatula, the crystals were removed from the flask and placed in a small vial, where they were washed in n-pentane using a digital sonifier.

Figure 3:
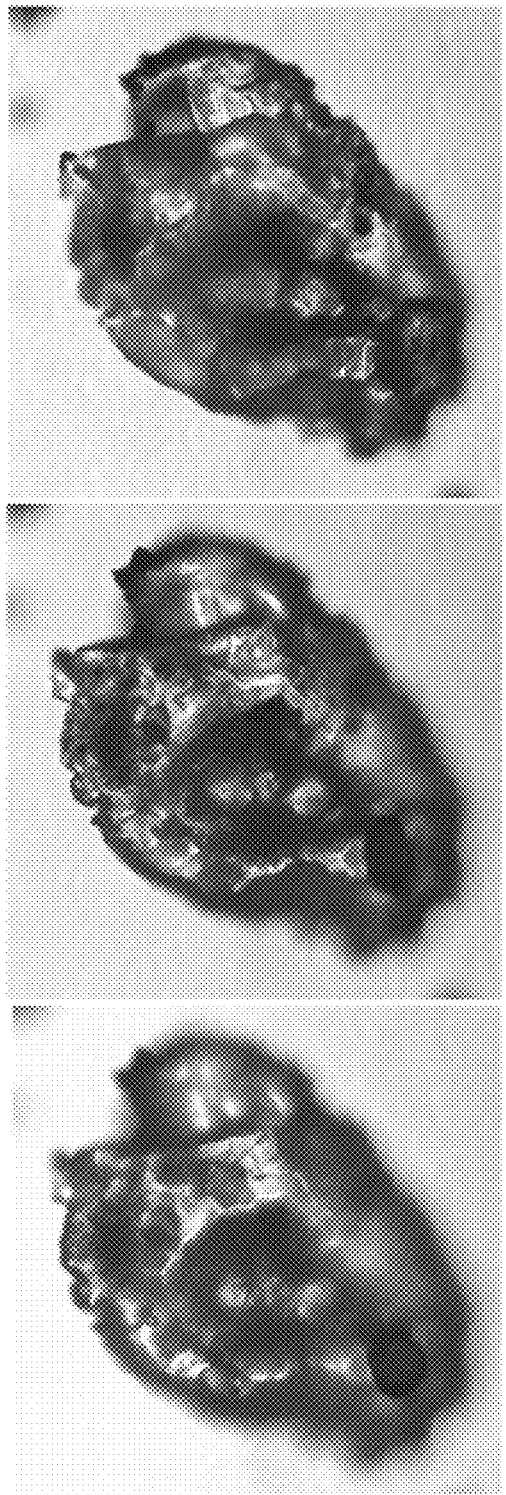
FIG. 3 is a series of microscopic photos of an example crystal, as produced using a method described herein.

A typical crystal from this example is shown in FIG. 3. The focal plane of the microscope moves from the bottom, to middle, to the top of the crystal across the series shown in FIG. 3. Since the nanometric iron oxide particle is in focus at the center of the series, capture is indicated. For improved optical viewing, little effort was made to better disperse the particles, as fully disperse nanoparticles would be extremely difficult to see under the optical microscope.

Various compositions and materials can be made which incorporate the nanoparticles. This can be done generally by admixing or introducing the crystal-encapsulated nanoparticles into the composition or material.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for making a composite of nanometric particles encapsulated by crystals, said method comprising:
   crystallizing a solution comprising nanometric particles, a micelle-forming material, a nonpolar dispersant for the micelle-forming material and a crystal-forming material to form crystal-encapsulated nanometric particles.

2. The method of claim 1 wherein said nanometric particles comprise a nanometric particle selected from the group consisting of iron oxide (nanocat), nanoaluminum, nanoboron, boron-nitride nanotubes (BNNT), nanodiamond, and combinations of two or more thereof.

3. The method of claim 2 wherein said nanometric particles comprise iron oxide.

4. The method of claim 1 wherein said crystal-forming material comprises ammonium perchlorate.

5. The method of claim 1 wherein said micelle-forming material is hydroxyl terminated polybutadiene.

6. The method of claim 1 wherein said nonpolar dispersant comprises pentane.

7. The method of claim 1 wherein said crystallizing is carried out by drying.

8. The method of claim 1 wherein said micelle-forming material and said nonpolar dispersant are combined with a suitable solvent prior to said crystallizing.

9. The method of claim 8 wherein said crystal-forming material is added to the combination of said micelle-forming material, said nonpolar dispersant and said solvent.

10. The method of claim 9 wherein said crystal-forming material is a salt and said salt is substantially or completely dissolved in said solution.

11. The method of claim 10 wherein said dissolving is carried out by mechanical agitation or temperature change.

12. The method of claim 10 wherein said nanometric particles are added to said micelle-forming material, said nonpolar dispersant and said salt.

13. The method of claim 12 wherein said nanometric particles are dispersed in said polar solvent, said micelle-forming material, said non-polar dispersant, and said salt.

14. The method of claim 13 wherein said dispersion is carried out by mechanical agitation.

15. The method of claim 1 wherein nanometric iron oxide particles are encapsulated inside of micrometric ammonium perchlorate crystals, the method comprising:
   preparing a solution including nanometric iron oxide and ammonium perchlorate with a micelle-forming material and a polar dispersant for the micelle-forming material; and said crystallizing step comprises crystallizing the solution to form nanometric iron oxide particles encapsulated inside of micrometric ammonium perchlorate crystals.

16. The method of claim 15 wherein the micelle-forming material comprises hydroxyl terminated polybutadiene.

17. The method of claim 15 wherein said crystallizing is carried out by drying.

18. A method for making a core-shell composite material, said method comprising:
crystallizing a solution comprising nanometric particles, a micelle-forming material, a nonpolar dispersant for the micelle-forming material and a crystal-forming material to form the core-shell composite material wherein nanometric particles form a core within a micron-sized crystal shell.

* * * * *